(12) United States Patent
Lum et al.

(10) Patent No.: US 10,576,209 B2
(45) Date of Patent: *Mar. 3, 2020

(54) SYRINGE ASSEMBLY HAVING A FLEXIBLE OR SLIDABLE FLANGE

(71) Applicant: Becton Dickinson France, Le Pont-de-Claix (FR)

(72) Inventors: Chee Leong Lum, Pequannock, NJ (US); Eric Schiller, Kinnelon, NJ (US)

(73) Assignee: Becton Dickinson France, Le Pont-de-Claix (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/145,274

(22) Filed: Sep. 28, 2018

(65) Prior Publication Data

US 2019/0030252 A1  Jan. 31, 2019

Related U.S. Application Data

(63) Continuation of application No. 14/163,381, filed on Jan. 24, 2014, now Pat. No. 10,112,014, which is a continuation of application No. 12/859,521, filed on Aug. 19, 2010, now abandoned.

(60) Provisional application No. 61/235,792, filed on Aug. 21, 2009.

(51) Int. Cl.
*A61M 5/31* (2006.01)
*A61M 5/315* (2006.01)

(52) U.S. Cl.
CPC ........ *A61M 5/3137* (2013.01); *A61M 5/31525* (2013.01); *A61M 5/31555* (2013.01); *A61M 2005/3139* (2013.01)

(58) Field of Classification Search
CPC ........ A61M 5/3137; A61M 2005/3139; A61M 2005/3142
See application file for complete search history.

(56) References Cited

U.S. PATENT DOCUMENTS

| | | | |
|---|---|---|---|
| 772,114 A | 10/1904 | Pappenheim |
| 801,912 A | 10/1905 | Rehmann |
| 1,130,493 A | 3/1915 | Dickinson |
| 1,142,682 A | 6/1915 | Dickinson |
| 1,155,012 A | 9/1915 | Slee |
| 1,331,805 A | 2/1920 | Chance |
| 1,526,056 A | 2/1925 | Eisele |
| 1,592,335 A | 7/1926 | Brody et al. |
| 1,644,901 A | 10/1927 | Stieglitz |

(Continued)

FOREIGN PATENT DOCUMENTS

| FR | 2830764 A1 | 4/2003 |
|---|---|---|
| JP | 18796 A | 11/1910 |

(Continued)

*Primary Examiner* — Shefali D Patel
(74) *Attorney, Agent, or Firm* — The Webb Law Firm (57) ABSTRACT

A syringe assembly having a flexible and/or slidable flange is provided, wherein in a pre-use or packaged state, the flange is positioned substantially parallel to a barrel of the syringe assembly resulting in the syringe assembly having a smaller packaging footprint. The smaller packaging footprint allows for a reduced storage space of the syringe assembly. Upon removal from a packaging and/or the storage space, the flange can be slid and locked into place such that the flange extends in a perpendicular direction with respect to a longitudinal axis of the barrel of the syringe assembly to allow for a traditional operation of the syringe assembly.

9 Claims, 8 Drawing Sheets

(56) References Cited

U.S. PATENT DOCUMENTS

| | | |
|---|---|---|
| 1,649,022 A | 11/1927 | Eisele |
| 1,798,116 A | 3/1931 | Brockway |
| 1,832,533 A | 11/1931 | Creasy |
| 1,834,713 A | 12/1931 | Kahn |
| 2,047,512 A | 7/1936 | Kauffman |
| 2,632,445 A | 3/1953 | Kas, Sr. |
| 2,823,675 A | 2/1958 | Sciurba |
| 2,829,643 A | 4/1958 | Debaz |
| 2,842,128 A | 7/1958 | Hein, Jr. |
| 2,854,975 A | 10/1958 | Cohen |
| 2,911,972 A | 11/1959 | Elinger |
| 3,039,468 A | 6/1962 | Price |
| 3,045,673 A | 7/1962 | Hein |
| 3,076,455 A | 2/1963 | McConnaughey et al. |
| 3,316,909 A | 5/1967 | Cowley |
| 3,384,082 A | 5/1968 | Harrold |
| 3,473,524 A | 10/1969 | Drewe |
| D228,970 S | 10/1973 | Cohen et al. |
| 3,978,858 A | 9/1976 | Tischlinger |
| 4,024,865 A | 5/1977 | Howlett |
| 4,068,661 A | 1/1978 | Hennings |
| 4,212,309 A | 7/1980 | Moorehead |
| 4,314,556 A | 2/1982 | Ma |
| 4,364,387 A | 12/1982 | Larkin |
| 4,540,405 A | 9/1985 | Miller et al. |
| 4,664,128 A | 5/1987 | Lee |
| 4,790,828 A | 12/1988 | Dombrowski et al. |
| 4,904,244 A | 2/1990 | Harsh et al. |
| 4,909,788 A | 3/1990 | Egolf |
| 4,927,416 A | 5/1990 | Tomkiel |
| 4,932,947 A | 6/1990 | Cardwell |
| 4,950,250 A | 8/1990 | Haber et al. |
| 4,990,135 A | 2/1991 | Truesdale, Jr. |
| 5,115,816 A | 5/1992 | Lee |
| 5,219,338 A | 6/1993 | Haworth |
| 5,250,031 A | 10/1993 | Kaplan et al. |
| 5,256,132 A | 10/1993 | Snyders |
| 5,282,792 A | 2/1994 | Imbert |
| 5,295,972 A | 3/1994 | Mischenko |
| 5,338,309 A | 8/1994 | Imbert |
| 5,348,544 A | 9/1994 | Sweeney et al. |
| 5,376,081 A | 12/1994 | Sapienza |
| 5,419,775 A | 5/1995 | Haffner et al. |
| 5,509,903 A | 4/1996 | Grendahl et al. |
| 5,554,133 A | 9/1996 | Haffner et al. |
| 5,582,595 A | 12/1996 | Haber et al. |
| 5,607,399 A | 3/1997 | Grimard et al. |
| 5,667,495 A | 9/1997 | Bitdinger et al. |
| 5,697,918 A | 12/1997 | Fischer et al. |
| 5,700,247 A | 12/1997 | Grimard et al. |
| D397,790 S | 9/1998 | Naganuma |
| 5,803,918 A | 9/1998 | Vetter et al. |
| 5,897,532 A | 4/1999 | Spallek et al. |
| 5,902,278 A | 5/1999 | Aguilar |
| 5,984,901 A | 11/1999 | Sudo et al. |
| 5,997,514 A | 12/1999 | Balestracci |
| D434,850 S | 12/2000 | Balestracci |
| 7,175,609 B1 | 2/2007 | Gray |
| 7,241,277 B2 | 7/2007 | Rimlinger et al. |
| D581,527 S | 11/2008 | Jansen |
| 2004/0267206 A1 | 12/2004 | Rimlinger et al. |
| 2005/0159709 A1 | 7/2005 | Wilkinson |
| 2009/0036839 A1 | 2/2009 | Phalen |
| 2009/0093787 A1 | 4/2009 | Barbour |

FOREIGN PATENT DOCUMENTS

| | | |
|---|---|---|
| JP | 09173451 A | 7/1997 |
| JP | 2005530597 A | 10/2005 |
| JP | 2008503296 A | 2/2008 |
| JP | 2009526575 A | 7/2009 |
| WO | 8904681 A1 | 6/1989 |

SYRINGE ASSEMBLY HAVING A FLEXIBLE OR SLIDABLE FLANGE

CROSS REFERENCE TO RELATED APPLICATIONS

This application is a continuation of U.S. application Ser. No. 14/163,381 entitled "Syringe Assembly Having a Flexible or Slidable Flange" filed Jan. 24, 2014, which is a continuation of U.S. application Ser. No. 12/859,521 entitled "Syringe Assembly Having a Flexible or Slidable Flange" filed Aug. 19, 2010 which claims priority to U.S. Provisional Patent Application Ser. No. 61/235,792 entitled "Syringe Assembly Having a Flexible or Slidable Flange" filed Aug. 21, 2009, the entire disclosures of each of which are hereby incorporated by reference.

BACKGROUND OF THE INVENTION

Field of the Invention

The present invention is directed to a syringe assembly having a flexible and/or slidable flange, and more particularly, to a syringe assembly having a flexible and/or slidable flange having a smaller packaging footprint allowing for reduced storage space.

Description of Related Art

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depressing the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has a smaller packaging footprint, to reduce the storage space required for containing this syringe. It is also desirable to produce syringes that are uniform in terms of an outer surface shape to allow for stacking of the syringes within the storage cabinet.

SUMMARY OF THE INVENTION

In accordance with an embodiment of the present invention, a syringe assembly includes a flexible flange. The flexible flange comprises a first and second member wherein each of the members is disposed at least partially about a syringe barrel. The first member is disposed adjacent a proximal end of a syringe barrel and the second member is disposed about the syringe barrel a predetermined distance away from the first member along the syringe barrel. At least one flexible finger extends between and connects the first and second members at first and second connecting points. At least one bend point is provided on the at least one flexible finger. This at least one bend point is located between the first and second connecting points such that application of a force to the flexible finger and/or the second member causes the flexible finger to collapse and form a flange at the proximal end of the syringe barrel. According to one design of the flexible flange, the at least one flexible finger comprises a plurality of flexible fingers positioned around the syringe barrel. According to an alternative design, the at least one flexible finger comprises a pair of flexible fingers positioned at opposite sides of the syringe barrel. The flexible fingers can comprise a first and second portion separated by the at least one bend point so that the application of the proximal force causes the bend point to extend in an outward direction with respect to the barrel and the first and second portions are positioned adjacent with one another to form the flange.

In accordance with another embodiment, a syringe assembly includes a pair of circular members configured for placement about a syringe barrel wherein the circular members are positioned a predetermined distance away from each other along the length of the syringe barrel. At least one flexible finger is provided that extends between and connects the pair of circular members. The at least one flexible finger is configured for collapsing upon itself upon the application of a sliding force to either the at least one flexible finger or the at least one of the circular members to form a flange on the syringe barrel. The at least one flexible finger includes at least one bend point that allows the flexible finger to collapse upon itself upon the application of a sliding force. This at least one bend point can include a living hinge.

In accordance with another embodiment, the syringe assembly includes a syringe barrel having a proximal end and distal end wherein the distal end includes an outlet portion. A flexible flange is positioned about the syringe barrel and comprises at least a pair of circular members configured for placement about the syringe barrel. At least one of the circular members is positioned adjacent the proximal end of the syringe barrel and at least a second circular member is positioned a predetermined distance along the length of the syringe barrel away from the at least one circular member located at the proximal end of the syringe barrel. At least one flexible finger extends between and connects the pair of circular members. The at least one flexible finger is configured for collapsing upon itself upon the application of a sliding force to one of the at least one flexible finger and/or at least one of the circular members to form a flange at the proximal end of the syringe barrel. According to one embodiment, the at least one flexible finger includes at least one bend point to allow the flexible finger to collapse upon itself upon the application of a sliding force thereto. The syringe assembly can include a plunger rod and a plunger positioned within the syringe barrel. The plunger rod can include indicia thereon to allow for metered dosing. According to another embodiment, the plunger rod and plunger can be contained within the barrel and the flexible flange remains in a collapsed position for packaging.

In accordance with another embodiment, a syringe assembly includes a slidable flange having a flange member having a first end and a second end. An aperture is provided that extends through the flange member. This aperture is configured for placement of the flange member about a syringe barrel such that the first end of the flange member is positioned adjacent to a proximal end of the syringe barrel and the second end of the flange member extends toward a distal end of the syringe barrel in a pre-use position. The application of a force to the flange member causes the second end of the flange member to slide along the syringe barrel toward the proximal end of the syringe barrel. A locking member is provided at the proximal end of the syringe barrel such that a portion of the flange member can be snapped into place in the locking member to create a flange extending in a perpendicular direction with respect to a longitudinal axis of the syringe barrel. The locking member can comprise an undercut portion at the proximal end of the syringe barrel. The flange member can comprise an elongated member defined by sidewall portions connecting the first and second ends, and the aperture extending through the flange member can be oval in shape. The sidewall portions of the flange member can be configured to fit within the undercut portion of the locking member to lock the flange member in place. According to one embodiment, the flange member extends at an approximately 30° angle toward the distal end of the syringe barrel in the pre-use position and, upon assembly and securement to the locking member, can extend in a perpendicular direction with respect to the syringe barrel.

In accordance with yet another embodiment, a syringe assembly includes a slidable flange. The syringe assembly includes a syringe barrel having a proximal end and distal end. The distal end includes an outlet portion. The slidable flange is positioned about the syringe barrel and includes a slidable flange member having a first end and a second end. An aperture extends through the flange member and is configured for placement of the flange member about the syringe barrel such that the first end of the flange member is positioned adjacent to a proximal end of the syringe barrel, and the second end of said flange member extends toward a distal end of the syringe barrel in a pre-use position, wherein the aperture allows the second end of the flange member to slide along the length of the barrel toward the proximal end thereof upon the application of a force thereto. A locking member is provided at the proximal end of the syringe barrel for locking the flange member into place to create a flange extending in a perpendicular direction with respect to the syringe barrel. According to one embodiment, the locking member is an undercut portion located at the proximal end of the syringe barrel. Preferably, the flange member is elongated in shape having sidewall portions connecting the first and second ends and the opening is oval in shape, such that locking of at least the sidewall portions of the flange member in place causes the first and second end portions to extend in opposite directions in a perpendicular direction with respect to the syringe barrel to create the flange.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

FIGS. 2B-2E are sequential perspective views of the flange formation and syringe actuation of a flexible flange arrangement according to the embodiment of FIG. 2A, wherein FIG. 2B shows the flange fingers partially collapsed, FIG. 2C shows the flange fingers fully collapsed to form the flange, FIG. 2D shows the plunger in a withdrawn position, and FIG. 2E shows the syringe assembly after the plunger has been actuated;

DESCRIPTION OF THE PREFERRED EMBODIMENTS

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 1:
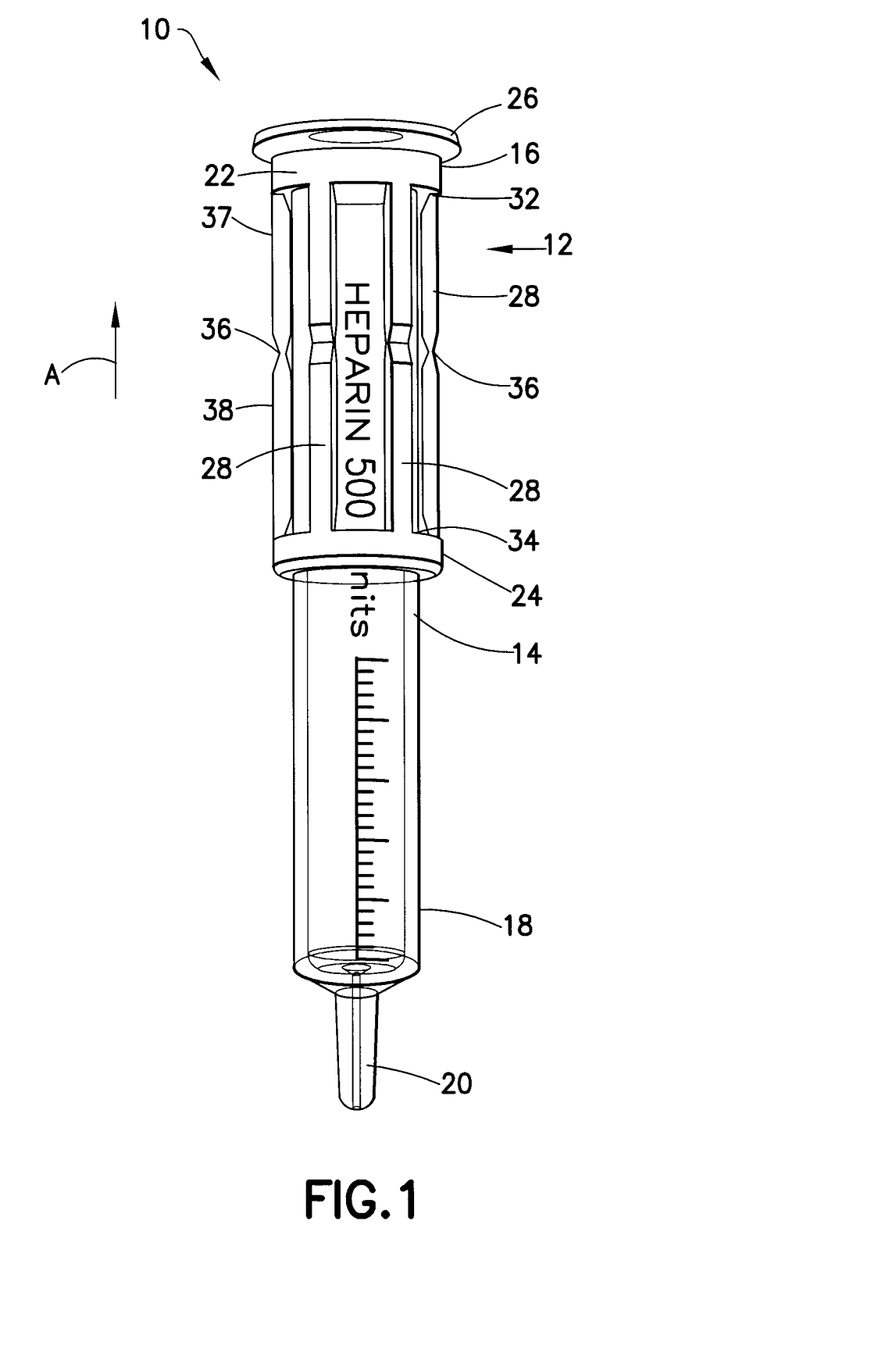
FIG. 1 is a perspective view of a syringe assembly including a flexible flange in accordance with an embodiment of the present invention.

As shown in FIG. 1, a syringe assembly, generally denoted as reference numeral 10, includes a flexible flange 12 in accordance with an embodiment of the present invention. The syringe assembly 10 includes a syringe barrel 14 having a proximal end 16 and distal end 18 and containing a fluid, such as a narcotic, diagnostic substance, or treatment substance, such as medication or a pain management substance therein. While described herein in terms of a filled or a pre-filled syringe, it is contemplated that syringe assembly 10 may be provided in a pre-filled state, or may be an empty syringe intended for filling immediately prior to use by the clinician. The distal end 18 includes an outlet opening 20, such as a luer tip or luer assembly for delivering the fluid stored within the syringe barrel 14 therethrough. This outlet opening 20 can be configured for attachment to a needle assembly, an intravenous connection system, or any variety of delivery systems.

The flexible flange 12 may include at least a first member 22 and a second member 24 disposed at least partially about the syringe barrel 14. In one embodiment, the first member 22 and the second member 24 have a profile that at least partially corresponds to an exterior surface of the syringe barrel 14 such that the first member 22 and the second member 24 may slide along the exterior surface of the syringe barrel 14. In a further configuration, the first member 22 and the second member 24 are substantially circular and are adapted to surround the exterior surface of the syringe barrel 14. In one embodiment, the first member 22 is configured for placement adjacent to the proximal end 16 of the syringe barrel 14. A stop member 26 can be provided at the proximal end 16 of the syringe barrel 14 to prevent the flange 12 from sliding off the barrel 14 during use of the syringe 10. The second member 24 may be configured for placement about the syringe barrel 14 at a predetermined distance away from the first member 22 along the length of the syringe barrel 14.

At least one flexible finger 28 extends between and connects the first and second members 22, 24 at first and second connecting points 32, 34. As shown in FIG. 1, a plurality of flexible fingers 28 can be provided between the first and second members 22, 24 which extend about the periphery of the syringe barrel 14.

At least one bend point 36 is provided on the at least one flexible finger 28. This at least one bend point 36 is located between said first and second connecting points 32, 34, preferably at a location midway between the first and second connecting points 32, 34. It is further contemplated that flexible fingers 28 may represent two or more separate pieces interconnected through a distinct hinge or other interconnecting member. For example, flexible fingers 28 may include first portion 37 and second portion 38 separated and interconnected with each other through a separate hinge element at bend point 36. In one particular embodiment, the separate discrete first and second finger portions 37, 38 are integrally formed, with bend point 36 representing a living hinge. The use of living hinges in the bend points 36 allows for the flexible fingers 28, 128 to flex to the ready position to create the flange 40. Thus, the bend point 36 can separate the at least one flexible finger 28, 128 into a first portion 37 and a second portion 38.

Bend points 36 can be any type of hinge member, such as a living hinge, over the center hinge, or a region adapted to fold, compress, or stack upon itself. In a further embodiment, the bend points 36 may include a mechanism for controlled or automated advancement of the flexible fingers 28 so as to cause first and second members 22, 24 to move toward each other about bend points 36. For example, it is contemplated that flexible fingers 28 may include a mechanism intended to impart a bias therein, such that flexible fingers 28 are biased into a hinged or folded state at bend points 36. In such an embodiment, a lock mechanism may be provided to maintain flexible fingers 28 in the first extended position, and upon release of the lock, flexible fingers 28 bend about bend points 36 toward and/or into the hinged or folded state. This may be accomplished by providing bend points 36 as an over the center type of hinge, wherein movement is initiated by the user by moving first and second members 22, 24 toward each other in the direction of arrow A, such as by moving second member 24 proximally, which movement may store potential energy within one or more of the hinges at bend points 36. Once bend points 36 reach a predetermined bent position, the stored potential energy within bend points 36 releases, to automatically complete the bending at bend points 36, thereby moving flexible fingers 28 into the fully bent position for use. In one embodiment, automation of the hinge or hinges at bend points 36 may be accomplished through a hinged arm interconnection as shown and described in U.S. Pat. No. 5,348,544 in connection with movement of a safety shield, the disclosure of which is incorporated herein by reference.

In a further embodiment, one or more extension spring members (not shown) may be provided interconnecting the first and second members 22, 24, for example, adjacent flexible fingers 28, for preloading the finger flange 12 in a biased state toward the ready position with flexible fingers 28 bent in the final state for use. In such an embodiment, the mechanism is prevented from automatically or prematurely bending since the bias of the applied force is to collapse the flexible fingers 28 inwardly, but is prevented from doing so by the wall of the syringe barrel 14. The user initiates the movement by moving first and second members 22, 24 toward each other in the direction of arrow A, such as by moving second member 24 proximally, which buckles the flexible fingers 28 outward, and the spring member (not shown) can then complete the bending of the flexible fingers 28 so as to place flexible flange 12 in the ready for use position.

Figure 2A:
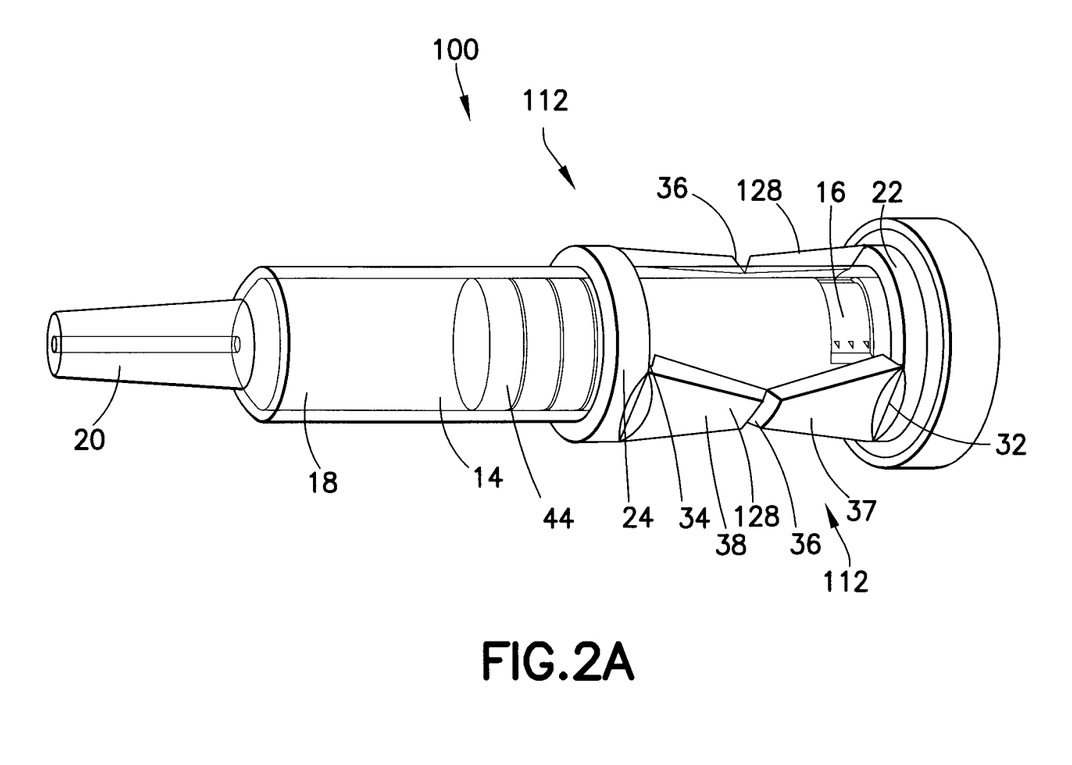
FIG. 2A is a perspective view of a syringe assembly in a pre-use position including a flexible flange according to an alternative design of the first embodiment of the invention.

As shown in FIG. 2A, in an alternative embodiment, a pair of flexible fingers 128 may be positioned on opposing sides of the syringe barrel 14 to form the flexible flange 112.

Reference is now made to FIGS. 2A-2E which show the sequential operation of the flexible flange 12, 112 of the invention. FIGS. 2A-2E show the functioning of the alternative design of flexible flange 112, however it is noted that flexible flange 12, according to the design shown in FIG. 1, would function in the same manner.

Figure 2B:
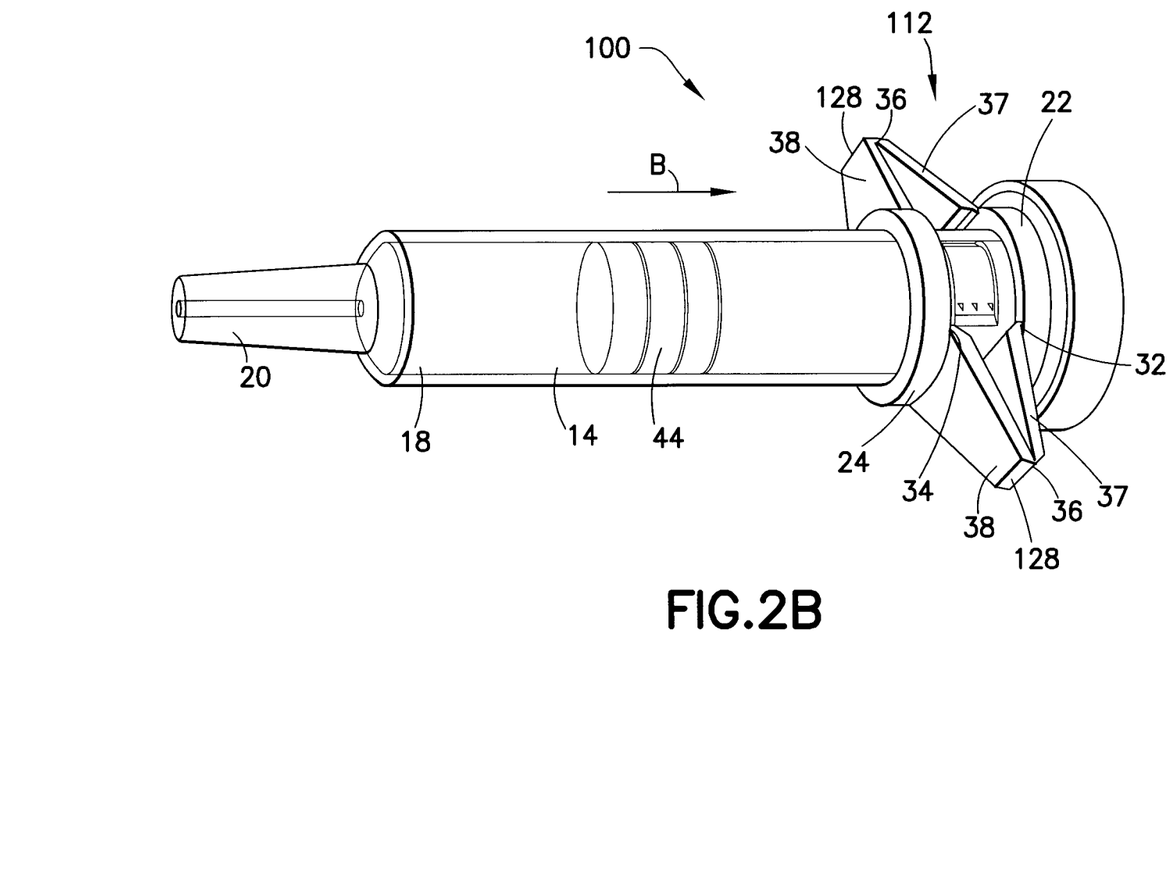
Figure 2C:
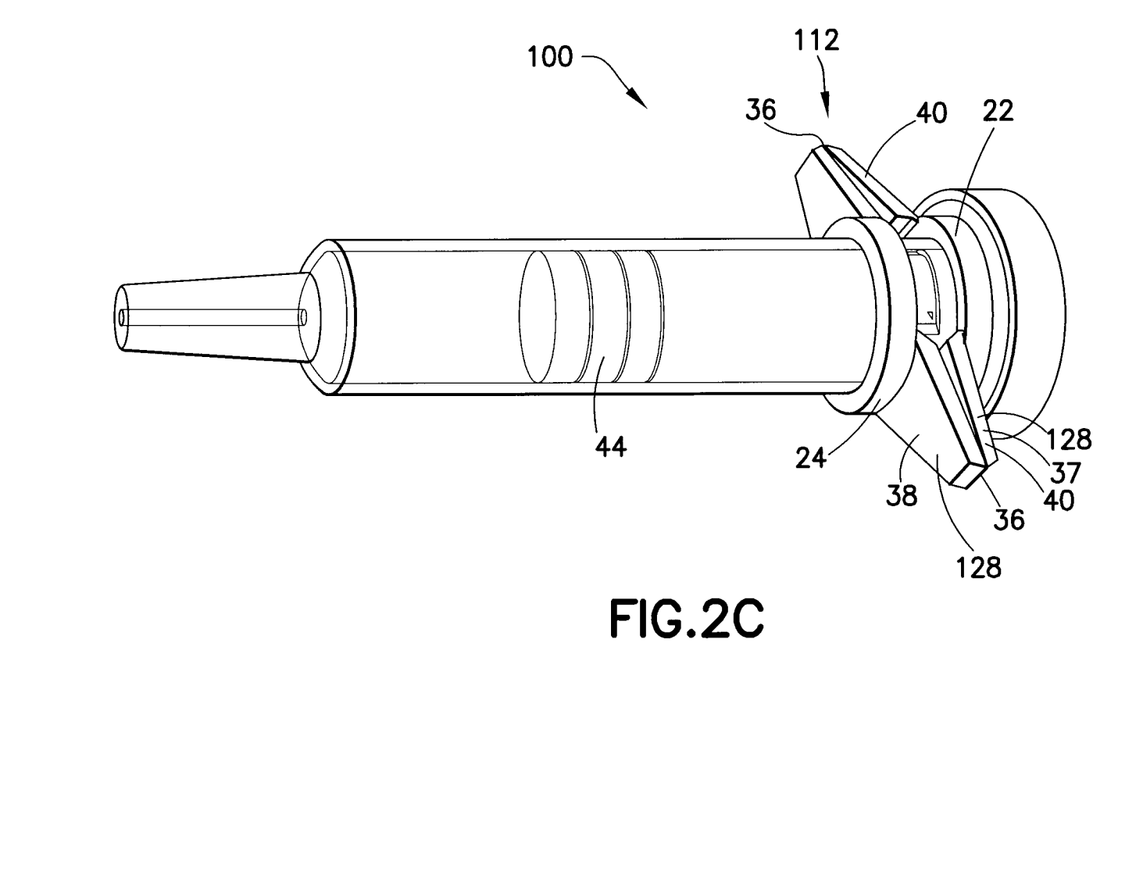

FIG. 2A shows the syringe assembly with the flange 112 in the pre-use position. It is this position in which the syringe assembly has the smallest footprint and is packaged for controlled storage thereof. In this configuration, the flexible flange 12, 112 is shown disposed along the syringe barrel 14 in the initial position. A fluid is disposed within the interior of the syringe barrel, and the plunger 44, having a plunger rod 42 connected thereto, is also disposed within the interior of the syringe barrel 14 in order to reduce the footprint of the overall syringe assembly 10. As shown in FIG. 2B, upon the application of a force to the flexible fingers 128 in the direction of arrow B, the second member 24 slides along the periphery of the syringe barrel 14 toward the proximal end 16 of the syringe barrel 14 causing the flexible fingers 128 to bend about bend point 36 and extend in an outward, perpendicular direction with respect to the syringe barrel 14. This force can be applied to either the second circular member 24 or a distal portion of the flexible fingers 128, as long as this force is applied between the bend point 36 and the second circular member 24 such as against the second portion 38 of the flexible finger 128. As shown in FIGS. 2B-2C, the application of a continued force in the direction of arrow B causes the flexible fingers 128 to collapse about the bend point 36 to bring the first portion 37 and the second portion 38 of the flexible fingers 128 into contact with one another to form a flange 40 at the proximal end 16 of the syringe barrel 14. Although FIGS. 1 and 2A show a flexible flange which can create a pair of flanges 40 at opposed ends of the syringe barrel 14, it is appreciated that a flexible finger arrangement can be provided so that only a single flange is created at one side of the syringe barrel 14, resulting in a reduction of materials and production costs.

Figure 2D:
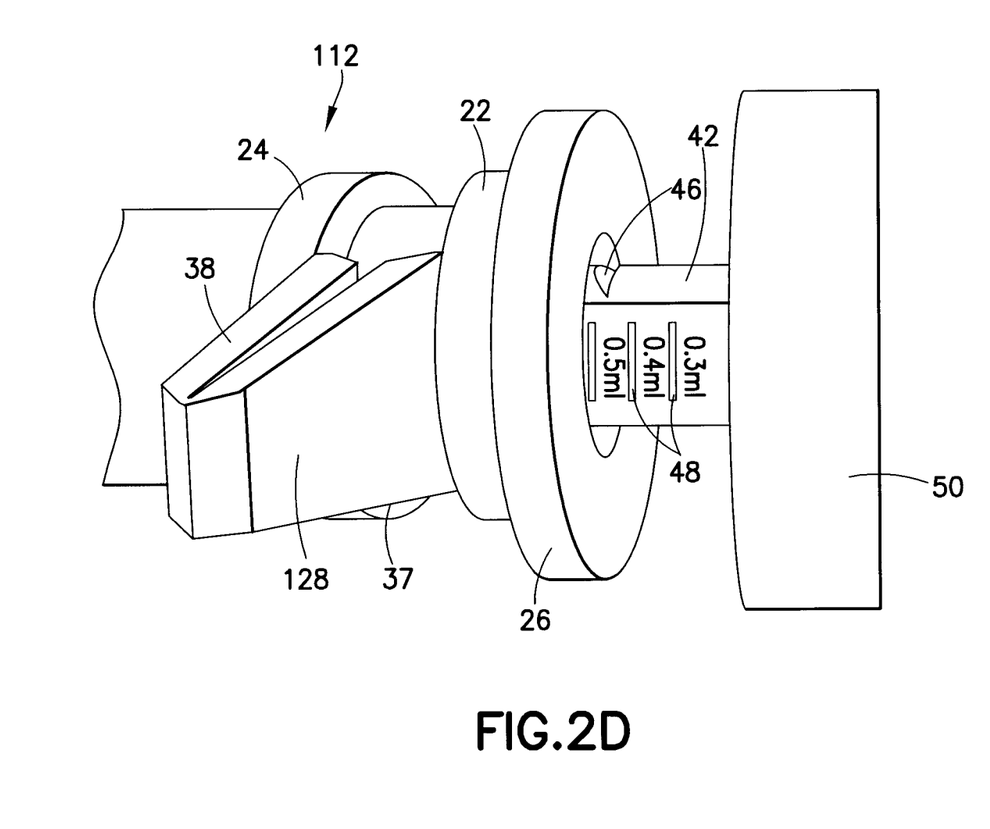
Figure 2E:
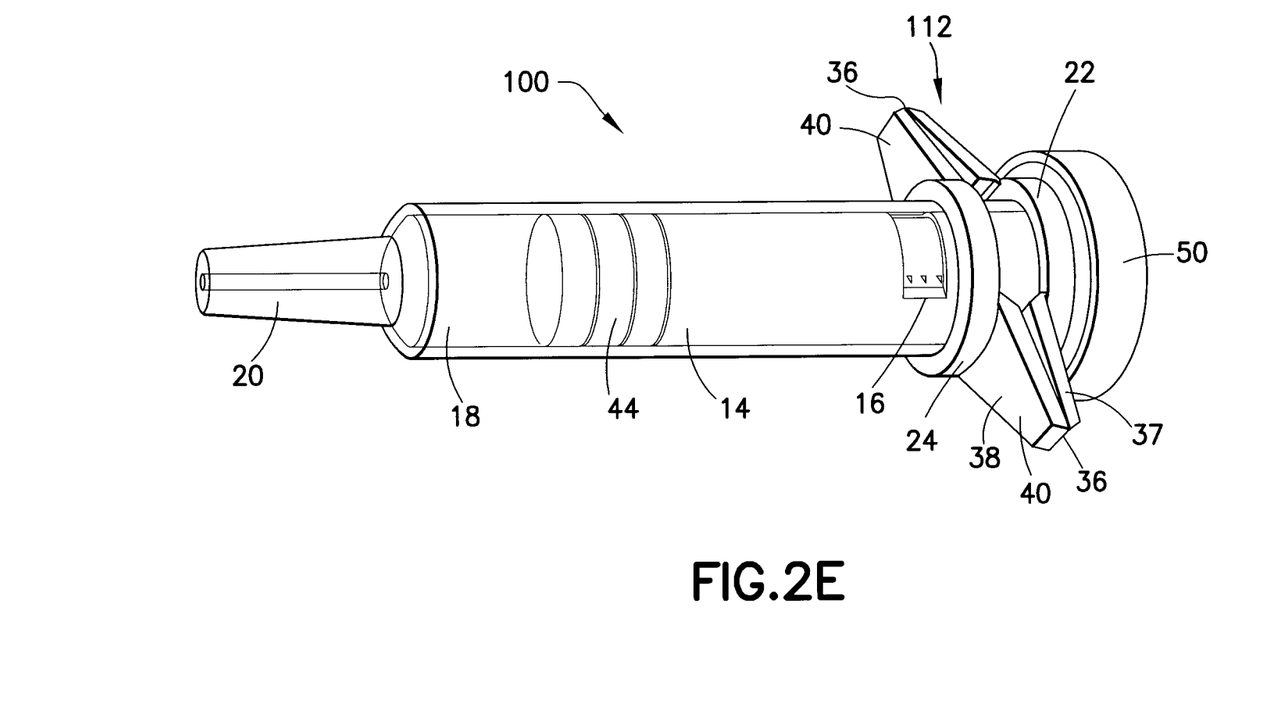

With reference to FIG. 2D, upon creation of the flanges 40, the syringe is ready for use and the plunger rod 42 attached to plunger 44 (shown in FIGS. 2A-2C) can be withdrawn from within the interior of the barrel 14 by the application of force to thumb press 50. Alternatively, a spring-loaded push button (not shown) may be deployed to automatically advance the plunger rod 42 from within the interior of the syringe barrel 14 in a proximal direction. According to one design, this plunger 44 can include a retention notch 46 and indicia 48 such as for use with a metered plunger assembly. Stop 26 prevents the flange 112 from being pulled off the syringe barrel 14 upon the application of the force thereto and during use of the syringe 10. Upon deployment of the thumb press 50, the plunger 44 and associated plunger rod 42 may be re-advanced into the interior of the syringe barrel 14 to expel the fluid contents from therein.

In a further configuration, the plunger 44 forms a liquid impermeable seal with a portion of the interior of the syringe barrel 14 for maintaining the fluid contents in an uncontaminated state. It is appreciated that the flexible flange 12 of the invention can be used with any type of syringe assembly 10, particularly those which are placed in a controlled storage environment in which storage space is limited. These types of syringes include traditional pre-filled syringe assemblies, collapsed plunger rod designs, metered dose syringes, and the like.

Figure 3A:
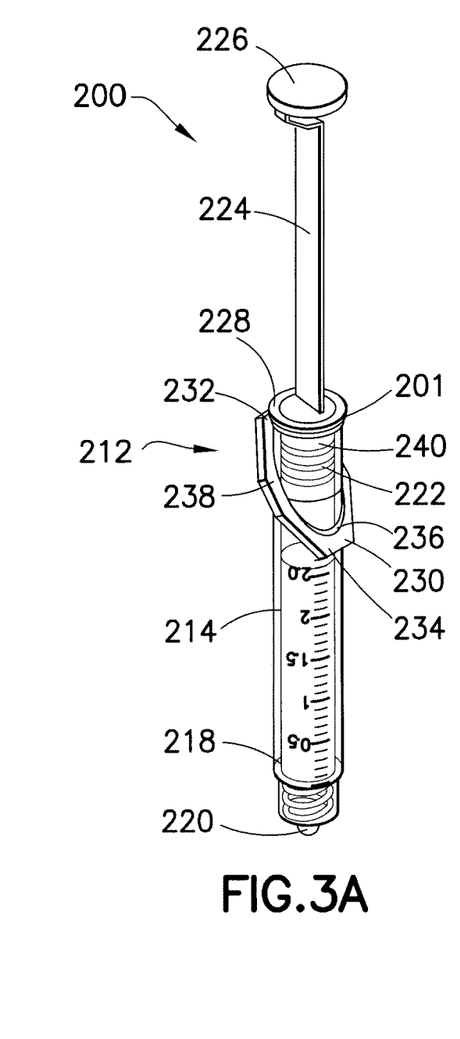
FIG. 3A is a perspective view of a syringe assembly having a sliding flange in an initial position in accordance with an embodiment of the present invention.
Figure 3B:
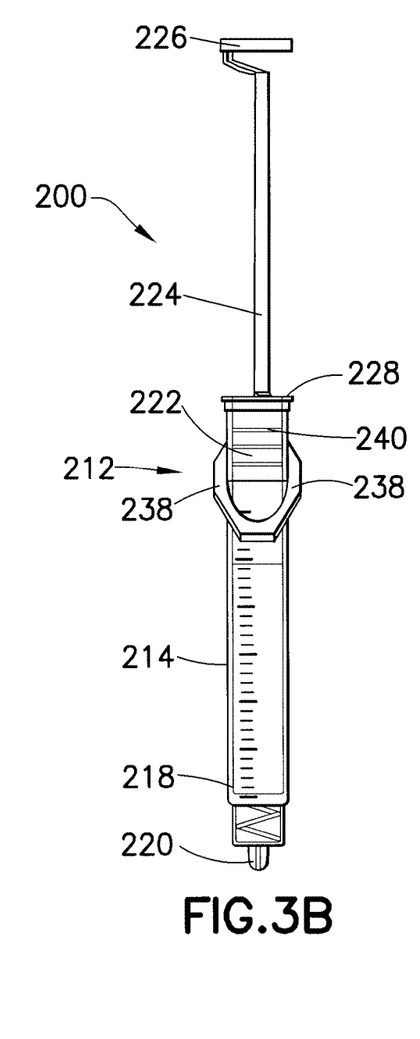
FIG. 3B is a front view of the syringe assembly of FIG. 3A.
Figure 3C:
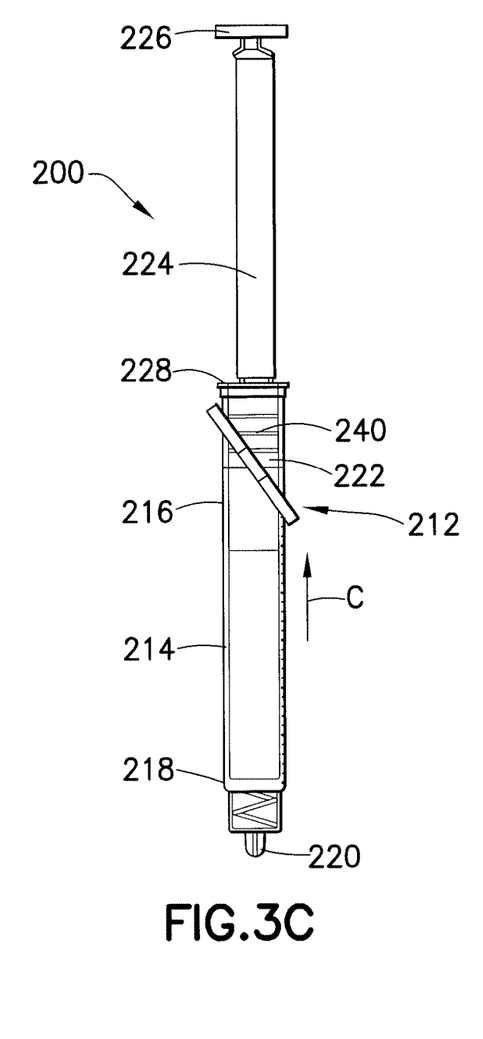
FIG. 3C is a left side view of the syringe assembly of FIG. 3A.

Reference is now made to FIGS. 3A-3C which show a syringe assembly 200 including a sliding flange 212, according to another embodiment of the present invention. The flange member 230 may include an elongated member defined by sidewall portions 238 connecting the first and second ends 232, 234 and an aperture 236 defined therein. As discussed above, the syringe assembly 200 can include any known type of syringe and is preferably of the pre-filled variety which is typically stored in a locked cupboard to prevent theft of the contents therein or even the syringe assembly itself. Typically, the syringe 200 includes a syringe barrel 214 having a proximal end 216 and distal end 218. The distal end 218 includes an outlet opening 220, such as a luer assembly as discussed herein. For packaging purposes, this outlet opening 220 is typically closed by a closure or cap (not shown), as is well known in the art. The syringe 200 may also include a plunger 222, having a plunger rod 224 connected thereto, and a thumb press member 226 connected to the plunger rod 224, as is also common in the art. The plunger rod 224 may or may not be disposed or partly contained within the syringe barrel 214 in a pre-use, packaged state.

The slidable flange 212 may include a flange member 230 having a first end 232 and a second end 234. An aperture 236 is provided which extends through the flange member 230. This aperture 236 is configured to allow the syringe barrel 214 of the syringe assembly 200 to be disposed therethrough. In one embodiment, the aperture 236 is substantially oval in shape, but may be rectangular, round, square, or any other shape. The substantially oval aperture 236 has a first diameter extending along a minor axis of the aperture 236 that is smaller than a second diameter extending along a major axis of the aperture 236, where the minor axis is coplanar with and perpendicular to the major axis. As shown in FIG. 3A, the major axis of the aperture 236 extends across the aperture 236 between the first end 232 of the flange member 230 and the second end 234 of the flange member 230. As illustrated in FIGS. 3A-3C, the aperture 236 is configured for placement of the flange member 230 about the syringe barrel 214 such that the first end 232 of the flange member 230 is positioned adjacent to the proximal end 216 of the syringe at a first distance from the distal end 218 of the syringe barrel as measured in a direction parallel to a longitudinal axis of the syringe barrel, and the second end 234 of the flange member 230 extends toward the distal end 218 of the syringe barrel and is at a second distance from the distal end 218 of the syringe barrel as measured in a direction parallel to the longitudinal axis of the syringe barrel in a pre-use position. The first distance is greater than the second distance as shown in FIG. 3A. A stop member 228 may be provided on a proximal end 216 of the syringe barrel 214 to prevent the slidable flange 212 from being separated from the syringe barrel 214 in a proximal direction. The stop member 228 may have any suitable configuration—such that the interior of the aperture 236 is dimensioned to be restrained by the stop member 228 to prevent the slidable flange 212 from being advanced over the stop member 228. The slidable flange 212 may also be restrained from separating or tilting away from the syringe barrel 214 in the distal direction by a similar stop member or other restraining mechanism which limits movement of the first end 232 of the slidable flange 212. For example, dimensional geometries may provide for an interference fit between the aperture 236 of the slidable flange 212 and the wall of the syringe barrel 214, in particular with the minor axis of the oval of aperture 236 providing the points of contact for interference fit with the wall of syringe barrel 214. In embodiments in which the aperture is rectangular shaped, such interference constraint may be provided across the minor axis of the rectangular opening. In certain embodiments, the first end 232 of the slidable flange is fixed with respect to the syringe barrel 214 and the second end 234 of the slidable flange 212 is unrestrained.

Figure 4A:
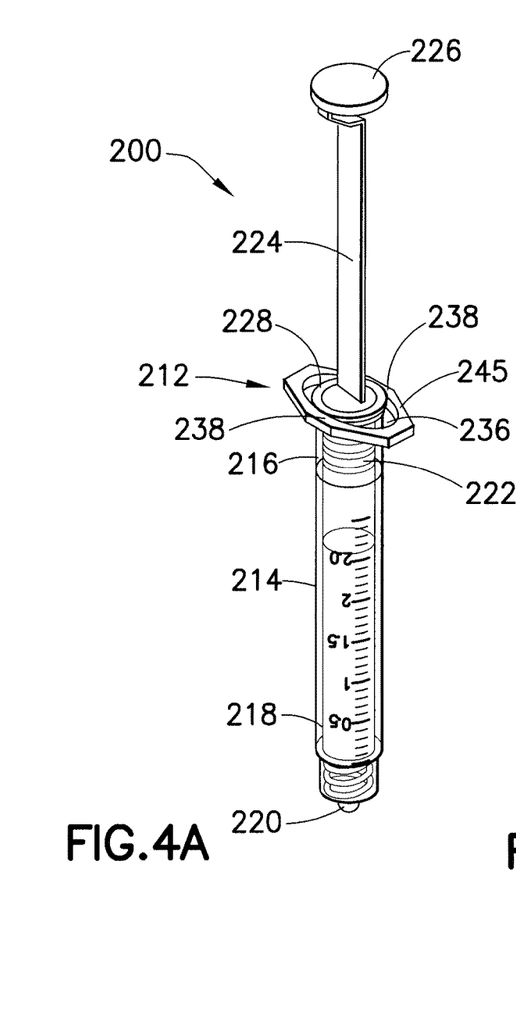
FIG. 4A is a perspective view of the syringe assembly of FIG. 3A having a sliding flange in a ready-to-use position in accordance with an embodiment of the present invention.
Figure 4B:
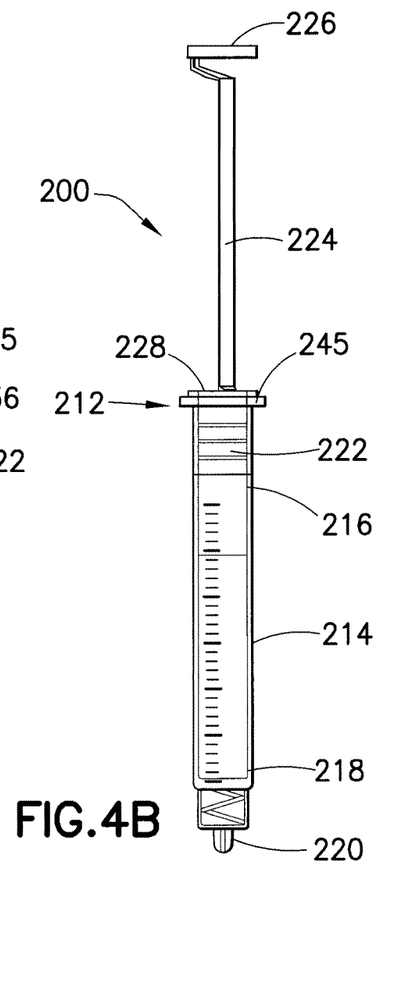
FIG. 4B is a front view of the syringe assembly of FIG. 4A.
Figure 4C:
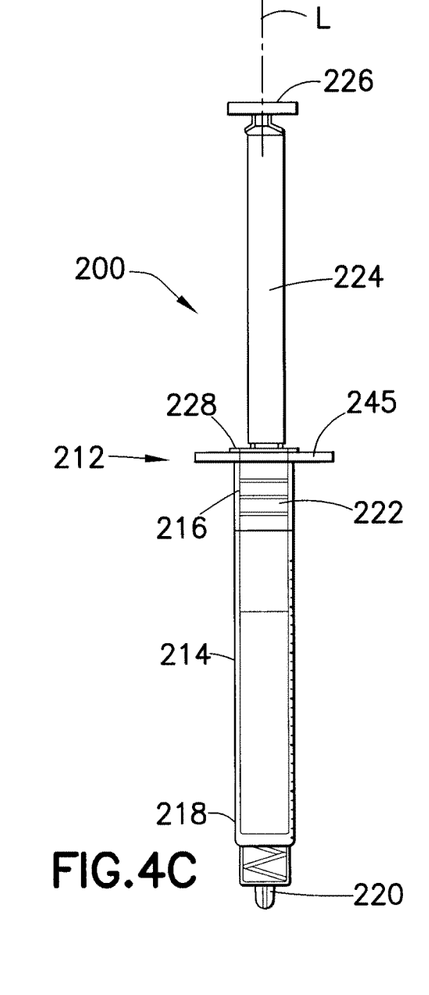
FIG. 4C is a left side view of the syringe assembly of FIG. 4A.

With continuing reference to FIGS. 3A-3C showing the slidable flange prior to assembly and to FIGS. 4A-4C showing the slidable flange after assembly, in operation, an application of a force is applied in a proximal direction to the flange member 230 to cause the second end 234 of the flange member 230 to slide along the syringe barrel 214 toward the proximal end 216 of the syringe 200 as shown by arrow C of FIG. 3C. A locking member 240, such as in the form of an undercut member, is provided at the proximal end 216 of the syringe barrel 214 such that a portion of the flange member 230, such as the sidewall portions 238, are snapped into place in the locking member 240 to create a flange 245 extending in a substantially perpendicular direction with respect to a longitudinal axis L of the syringe barrel 214, as shown in FIG. 4C.

In one embodiment, the aperture 236 may have a substantially oval interior shape in order to allow for the sidewall portions 238 to fit within the locking member 240 in the ready-to-use position, and to allow the slidable flange 212 to be disposed about the syringe barrel 214 at an angle in the initial position. Accordingly, the slidable flange 212 may be disposed in a substantially perpendicular orientation with respect to the syringe barrel 214 in the ready-to-use position, and may be disposed substantially along the syringe barrel 214 in the initial position, thus reducing the footprint of the syringe assembly 200 in the initial packaged position. In a further embodiment, the aperture in the flange may be substantially circular, and the receiving undercut may be substantially elliptical, such that the minor axis of the undercut provides the point of interference with the circular aperture in the flange to lock the flange in place with respect to the syringe barrel.

According to one configuration, the flange member 230 and aperture 236 can be designed such that the flange member 230 extends at an approximately 30° angle toward the distal end 218 of the syringe barrel 214 in the pre-use packaged position and extends in a perpendicular direction with respect to the syringe barrel 214 after securement by the locking member 240. It is appreciated that the flange member 230 and aperture 236 can have a variety of shapes and/or forms and include a single end member or multiple end members depending upon the desired final shape of the flange 245. It is also appreciated that the flange member 230 can be formed from any well known material.

It can be appreciated that the flexible and/or slidable flange of the invention locks in place during use and can then be unlocked or unassembled to its initial position where the flange extends substantially parallel with respect to the syringe body to allow for a reduced footprint in a sharps disposal container.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

The invention claimed is:

1. A syringe assembly comprising:
a syringe barrel having a proximal end and a distal end, said distal end including an outlet portion; and
a slidable flange positioned about the syringe barrel, said slidable flange comprising:
a slidable flange member having a first end and a second end; and
an aperture extending through said slidable flange member,
wherein the slidable flange is transitionable from a first pre-use position to a second use position and in the pre-use position, the entirety of the flange member is angled with respect to a longitudinal axis of the syringe barrel such that the first end of the flange member is farther from the distal end of the syringe barrel than the second end of the flange member and, in the second use position, the first end of the flange member and the second end of the flange member are equidistant from the distal end of the syringe barrel and the flange member creates the flange extending in a perpendicular direction with respect to the longitudinal axis of the syringe barrel, and
wherein the aperture allows the second end of said slidable flange member to slide along a length of the syringe barrel toward the proximal end thereof upon an application of a force thereto.

2. The syringe assembly of claim 1, further comprising a locking member provided at the proximal end of the syringe barrel for locking the slidable flange member with respect to the syringe barrel.

3. The syringe assembly of claim 2, wherein the locking member is an undercut portion located at the proximal end of the syringe barrel.

4. The syringe assembly of claim 1, wherein, in the pre-use position, the first end of the slidable flange member is positioned adjacent to the proximal end of the syringe barrel and the second end of the slidable flange member extends toward the distal end of the syringe barrel.

5. The syringe assembly of claim 1, wherein a first diameter of the aperture extending along a minor axis of the aperture is smaller than a second diameter of the aperture extending along a major axis of the aperture, the minor axis being coplanar with and perpendicular to the major axis.

6. The syringe assembly of claim 5, wherein the major axis of the aperture extends across the aperture between the first end and the second end of the slidable flange member.

7. The syringe assembly of claim 1, wherein the slidable flange member comprises an elongated portion having sidewall portions connecting said first and second ends and the aperture is oval in shape.

8. The syringe assembly of claim 7, wherein locking of at least the sidewall portions of the slidable flange member causes the first and second ends to extend in opposite directions in the perpendicular direction with respect to the syringe barrel to create the flange.

9. The syringe assembly of claim 1, wherein, in the pre-use position, the first end of the slidable flange member is fixed with respect to the syringe barrel.

* * * * *